United States Patent [19]

Pomeranz

[11] 4,432,357
[45] Feb. 21, 1984

[54] CONDOM WITH RHEOPEXIC FILLED DEFORMABLE CHAMBER

[76] Inventor: Mark L. Pomeranz, 9760 Viceroy Dr. East, Jacksonville, Fla. 32217

[21] Appl. No.: 388,107

[22] Filed: Jun. 15, 1982

[51] Int. Cl.³ .............................................. A61F 5/00
[52] U.S. Cl. ..................................... 128/79; 604/327; 604/346; 604/349; 128/132 R
[58] Field of Search ..................... 128/79, 132 R, 1 R; 604/327, 328, 330, 335, 346, 347, 349, 351

[56] References Cited

U.S. PATENT DOCUMENTS

| 2,586,674 | 2/1952 | Lönne ........................... 128/132 R |
| 4,224,933 | 9/1980 | Reiling .................................. 128/79 |
| 4,353,360 | 10/1982 | Finney et al. ......................... 128/79 |
| 4,378,792 | 4/1983 | Finney .................................. 128/79 |

OTHER PUBLICATIONS

Appearance of Myelin Forms in Rheopexic Dispersion of Dioctyl Sodium Sulfosuccinate, Levinson et al., Journal of Phamaceutical Sciences, vol. 65, No. 8, Aug. 1976, pp. 1265-1266.
'Rheological Characterization of Dioctyl Sodium Sulfosuccinate in Normal Saline and Distilled Water', Journal of Colloid and Interface Science, vol. 56, No. 2, Aug. 1976, p. 388-390.
'Effect on pH on Rheopexic Dispersion of Dioctyl Sodium Sulfo-Sulfosuccinate Dispersal in Normal Saline', Levinson et al., Journal of Colloid and Interface Science, vol. 72, No. 1, Oct. 15, 1979 pp. 159-160.

*Primary Examiner*—C. Fred Rosenbaum
*Assistant Examiner*—J. L. Kruter
*Attorney, Agent, or Firm*—Frishauf, Holtz, Goodman & Woodward

[57] ABSTRACT

A condom having a plurality of deformable sealed chambers along at least a portion of the length thereof, rheopexic fluid being filled in the deformable sealed chambers. When the chambers are deformed during use of the condom, shear stress is applied to the rheopexic fluid due to deformation of the sealed chambers to cause the rheopexic fluid to increase its consistency as a function of increasing shear stress applied thereto, thereby providing a stiffening effect to the condom.

17 Claims, 7 Drawing Figures

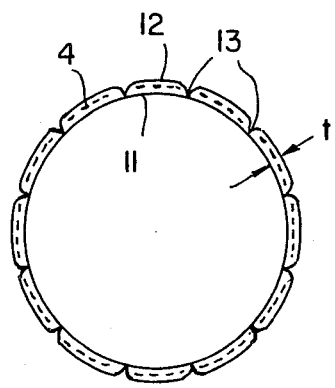
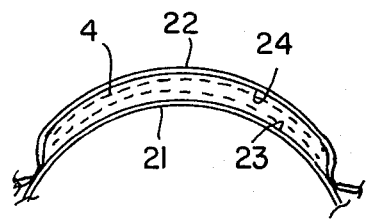
FIG. 5    FIG. 6
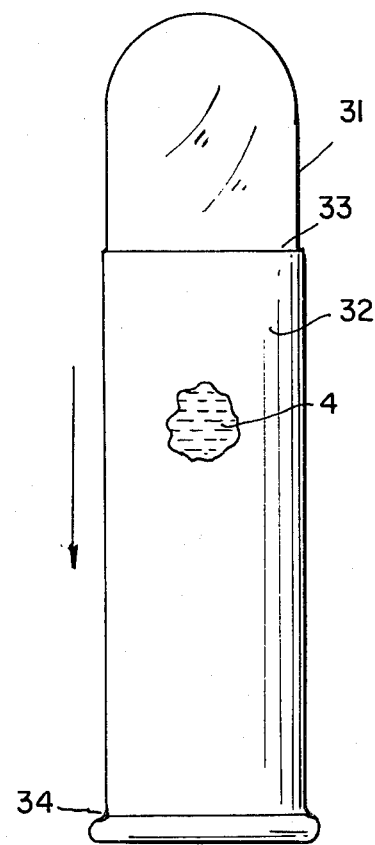
FIG. 7

CONDOM WITH RHEOPEXIC FILLED DEFORMABLE CHAMBER

BACKGROUND OF THE INVENTION

This invention relates to condoms, and more particularly to a condom having a stiffening characteristic.

The condom of the present invention incorporates rheopexic fluids, which are known per se. A discussion of rheopexic fluids is given hereinbelow to facilitate an understanding of the present invention.

A rheopexic fluid is a material which thickens with increasing shear stress and remains at the thicker consistency for a period of time before returning to the original consistency which is of a lower viscosity. The increase of thickness or viscosity results from application of shear stress which can be applied in the form of agitation such as repeated applications of pressure.

The object of the present invention is to provide an improved condom using rheopexic fluid, which provides a stiffening effect for the user.

SUMMARY OF THE INVENTION

According to the invention, a condom comprises: an elongated generally tubular member of thin, flexible material, said tubular member having a closed and open end; means defining a plurality of deformable sealed chambers along the length of at least a portion of the tubular member; and rheopexic fluid filled in the plurality of deformable sealed chambers such that when the deformable sealed chambers are deformed during use of the condom in intercourse, shear stress is applied to the rheopexic fluid due to deformation of the sealed chambers to cause the rheopexic fluid to increase its consistency as a function of increasing shear stress applied thereto, thereby providing a stiffening effect to the condom.

BRIEF DESCRIPTION OF THE DRAWINGS

FIG. 5 is a sectional view taken along the line V—V in FIG. 4;

FIG. 6 is a sectional view of a modified embodiment of the device of FIG. 1 using laminated materials; and FIG. 7 illustrates a further embodiment of the invention.

DETAILED DESCRIPTION

Figure 1:
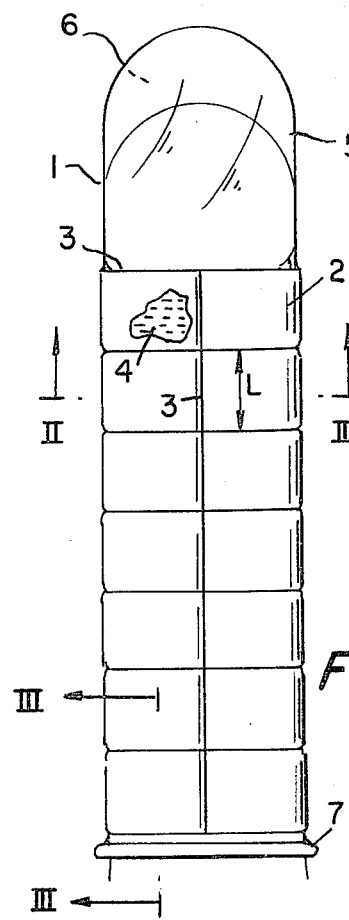
FIG. 1 is a side view of a first embodiment of a condom according to the present invention.

The rheopexic fluid used in the invention is preferably an aqueous solution of a dialkyl sulfosuccinate salt of the formula

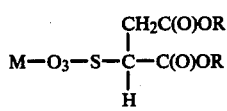

wherein R is an alkyl group containing 6 to 12 carbon atoms and preferably 8 to 12 carbon atoms with the octyl (e.g., 2-ethylhexyl) group being particularly preferred. M is a Group IA ion and preferably sodium, potassium or lithium, with sodium being particularly preferred. The 1,4-bis(2-ethylhexyl) sodium sulfosuccinate is the most preferred compound.

The aqueous solution is preferably a Normal saline solution (0.9 gram of sodium chloride in 100 milliliters of water) or a Ringer's solution (0.86 grams sodium chloride, 0.03 gram potassium chloride and 0.33 gram calcium chloride in 100 milliliters of water). These solutions are referred to as physiological electrolyte solutions or commonly physiological solution.

The solutions can contain from about 0.7 to 1.3 grams of the salt per 100 milliliters of water and preferably between about 0.8 and 0.10 grams. The range of between about 0.85 and 0.95 grams per 100 milliliters is particularly preferred.

The dialkyl (e.g., the 1,4-bis(2-ethylhexyl) sulfosuccinate salt is dissolved in the physiological solution in an amount between about 15 and 200 grams per 100 milliliters of solution and preferably in an amount between about 19 and 100 grams. The range of between about 19 and 65 grams is particularly preferred.

The rheopexic solution should have a pH of at least about 4 to exhibit the desired rheopexic characteristics. It preferably has a pH of at least about 5, with the range between about 5 and 7 being preferred. The effect of pH on rheopexic dispersions of dioctyl sodium sulfosuccinate in Normal saline are disclosed in an article by Levinson, Allen and Diagle in the Journal of Colloid and Interface Science, Vol. 72, No. 1, Oct. 15, 1979, pages 159-160.

Other characteristics of rheopexic dispersions of dioctyl sodium sulfosuccinate are disclosed in the Levinson, Allen and Diagle article in the Journal of Colloid and Interface Science, Vol. 56, No. 2, August 1976, pages 388-390, and in the Levinson, Allen, Vishnupad and Ecanow article in the Journal of Pharmaceutical Sciences, Vol. 65, No. 8, August 1976, pages 1265-1266.

The rheopexic solutions can be prepared by dissolving the dialkyl sulfosuccinate salt in the physiological solution. The salt may be in the form of a solid or in the form of a dispersion or solution in water or a water mixture, such as a water alcohol or water glycol mixture.

The preferred source of sodium dioctyl sulfosuccinate are the AEROSOL OT surfactants marketed by American Cyanamid. The preferred product is AEROSOL OT 100 which is a waxy solid sodium dioctyl sulfosuccinate. The OT 75 which contains about 75% of the solid salt and 25% of a mixture of water and alcohol and the OT 70 PG which contains about 70% of the solid salt with the remainder a mixture of water and propylene glycol also have provided useful rheopexic fluids when dissolved in the physiological solution.

The rheopexic effect is obtained over a wide temperature range between freezing and boiling with the range of 1.5° C. to 100° C. being preferred and the range of 1.5° C.-29° C. being particularly preferred.

The gel viscosity attained and the time during which the gel will remain in gel form after the applied stress is removed varies with the particular sulfosuccinate salt form used to prepare the rheopexic solution. A rheopexic solution prepared from OT-100 (100% solid salt) (1) attains a higher viscosity than a rheopexic solution prepared from OT-75, and (2) retains its gel viscosity for a longer time after the applied stress is removed.

The rheopexic fluid used in the embodiments exemplified herein was prepared by dissolving 19 parts by weight of solid powdery sodium 1,4-bis(2-ethylhexyl) sulfosuccinate (AEROSOL OT-100) in 100 ml. of Normal saline solution.

The rheopexic fluid described above is used in accordance with the present invention in condoms wherein the thickening effect of the rheopexic fluid under application of shear stress causes stiffening of the condom during use, thereby aiding the user in maintaining an erection.

Figure 2:
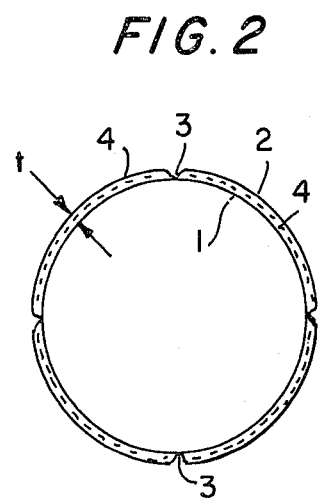
FIG. 2 is a line-type sectional view thereof taken along the line II—II in FIG. 1.
Figure 3:
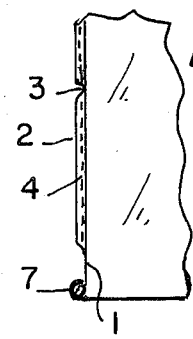
FIG. 3 is a sectional view taken along line III—III in FIG. 1.

FIGS. 1-3 illustrate a first embodiment of the condom in accordance with the present invention wherein the condom comprises inner and outer layers 1,2. Inner and outer layers 1,2 are sealed together, for example by heat sealing, at portions 3 to provide a plurality of chambers or compartments formed between the inner and outer layers 1,2. Rheopexic fluid 4 is contained within the chambers defined between the inner and outer layers 1,2. The area of the condom corresponding to the head of the penis does not have any chambers formed therein, and preferably forms only a single layer (either the outer layer 2 or the inner layer 1) so as to provide greatest sensitivity for the user. The single layer portion of the condom is indicated at 5 in FIG. 1. A space is provided at 6 above the head of the penis to contain the ejaculated semen. The bottom of the condom has a rubber band type portion 7 to provide a tight fit.

In use, shear stress is applied to the rheopexic fluid 4 contained within the various chambers or compartments defined between the inner and outer layers 1,2 under the effect of repeated movements carried out during sexual intercourse. As a result of the shear stress applied to the rheopexic fluid, the rheopexic fluid increases its consistency and becomes stiff, thereby simulating an erection, even if the user does not have a complete erection. Before the shear stress is applied to the rheopexic fluid, the rheopexic fluid is not viscous and is not stiff. After the application of shear stress, the viscosity of the fluid increases and the device becomes stiff. After the application of shear stress has ceased, the rheopexic fluid will revert back to its low viscosity, non-stiff state.

Figure 4:
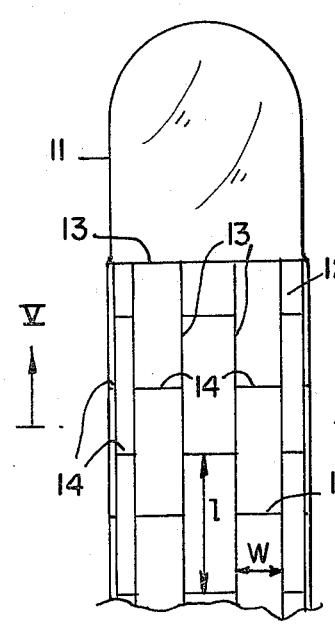
FIG. 4 is a side view of a modified embodiment of the present invention.

FIGS. 4 and 5 illustrate a modified embodiment of the present invention which uses the same rheopexic fluids as the embodiments of FIGS. 1-3, but wherein the arrangement of the chambers is modified. As illustrated in FIGS. 4 and 5, the condom comprises an inner layer 11 and an outer layer 12 which is sealed to the inner layer at portions 13, for example by heat sealing or other bonding techniques, depending upon the materials used. Section 11 is comprised of only the polymer material and contains no rheopexic fluid chamber. Rheopexic fluid 4 is contained within each of the chambers defined between inner and outer layers 11,12 by the sealing portions 13. As seen in FIG. 4, the chambers are elongated in the longitudinal direction of the condom, and are sub-divided in the elongated direction by horizontal sealing portions 14. Operation of the condom of FIGS. 4 and 5 is substantially similar to that of FIGS. 1-3, whereby stiffening characteristics are exhibited when the condom is placed under shear stress.

Generally, conventional condoms are made from lambskin and/or latex materials. However, while these materials are suitable for containing spermatozoa without leakage, it has been found that the rheopexic fluid is far less viscous in its unstressed state than the semen and could leak through lambskin and/or latex materials made of the thickness which is normally required for condom use. Therefore, inner and outer layers 1,2 and 11,12 of the device of the present invention are preferably made of copolymers of vinylidene fluoride and hexafluoropropylene such as the Viton copolymers marketed by Dupont and identified on page 1292 of the Merck Index, ninth edition. When Viton rubber, such as that described above, is used, single layers can be used for layers 1,2 and 11,12. The single layers can be, for example 1/32 inch thick, and the internal thickness of the respective chambers "t" (see FIGS. 2 and 5) is preferably approximately 1/16 inch, and substantially fully contained with rheopexic fluid. Other materials, such as polyethylene and polypropylene glycol could be used for the inner and outer layers of the condom of the present invention. Thin layers of polyethylene and/or polypropylene glycol of approximately 1/32 inch thickness would be fluid-tight to rheopexic fluid and would be sufficiently flexible for use in the condom, without leakage of rheopexic fluid or semen.

The overall length and inner diameter of the condom is conventional. In the embodiment of FIGS. 1-3, the height "h" of the respective chambers is approximately ½ inch, but other dimensions can be used, as desired. In the embodiment of FIG. 4, the width "w" of the respective chambers is preferably ¼ inch to ½ inch, and the length "l" of the respective chambers is preferably approximately one inch. While specific dimensions are given hereinabove, it should be clear that the dimensions are given by way of example only, and that various other dimensions can be used, as desired, depending upon characteristics required and the specific rheopexic fluid used.

In cases where lambskin and/or latex material are used for layers 1 and/or 2; 11 and/or 12, it is preferable that the layers be lined or laminated on the surfaces thereof interior of the respective chambers with Teflon or aluminum foil materials, such as shown in FIG. 6. FIG. 6 is an enlarged partial view of one of the chambers of the embodiment of FIGS. 1-3, and is a sectional view similar to FIG. 2. The inner layer 21 may be made of lambskin and/or latex, of a thickness generally used in condoms, and the outer layer 22 may be made of such lambskin and/or latex materials. Bonded to the surface of inner layer 21 which is interior of the chamber containing rheopexic fluid 4 is a layer 23 which may be Teflon or very thin aluminum foil, and a similar material is bonded or laminated to outer layer 22, as indicated by the reference numeral 24 in FIG. 6. While the terms laminating and/or bonding are used to define how the layers 21 and 23 are secured together, and how the layers 22 and 24 are secured together, any other method of adhesion can be used, so long as the result is to provide a firm bond and to provide a material which is not porous to the rheopexic fluid when it is in its most viscous or liquid state.

FIG. 7 illustrates a modified embodiment of the invention which does not contain any sub-divided chambers along the length of the condom. In use, rheopexic fluid contained in the single chamber defined between the inner and outer layers 31,32, respectively of the condom will be forced toward the base end of the condom near the shaft of the penis. Inner and outer layers 31,32 are sealed together at 33, the head end of the condom being a single layer 31. The layers are also sealed together at 34 to provide a single chamber between 33 and 34 and extending around the complete circumference of the condom, only the single chamber containing rheopexic fluid.

During use, the rheopexic fluid will be subjected to shear stress, will thicken and stiffen and will be forced toward the base end 34 of the condom. This will create pressure (by virtue of the flexibility and elasticity of the inner and outer layers) around the base end of the penis and will prolong the user's erection by prolonging the time required for disengorgement of blood vessels within the penis. This arrangement has an advantage that defined chambers are not provided along the length of the penis, thereby providing more sensitivity to the user. The device of FIG. 7 may be made from the same materials as the devices of FIGS. 1-6.

I claim:

1. A condom comprising:
   means defining an elongated generally tubular member of thin, flexible material, said tubular member having a closed and open end;
   means defining a plurality of deformable sealed chambers along the length of at least a portion of said tubular member; and
   rheopexic fluid filled in said plurality of deformable sealed chambers such that when said deformable sealed chambers are deformed during use of the condom in intercourse, shear stress is applied to said rheopexic fluid due to deformation of said sealed chambers to cause said rheopexic fluid to increase its consistency as a function of increasing shear stress applied thereto, thereby providing a stiffening effect to the condom.

2. The condom of claim 1, wherein said means defining said deformable sealed chambers comprises an outer layer around at least a portion of the length of said tubular member and being sealed to said tubular member at portions thereof to define said plurality of sealed chambers, said outer layer being of thin, flexible material.

3. The condom of claim 1 or claim 2, wherein said means defining said elongated tubular member and said means defining said plurality of chambers each comprise a thin, flexible layer of copolymers of vinylidene fluoride and hexfluoropropylene.

4. The condom of claim 1 or claim 2, wherein at least one of said means defining said tubular member and means defining said sealed chambers is made of lambskin.

5. The condom of claim 1 or claim 2, wherein at least one of said means defining said tubular member and means defining said sealed chambers is made of latex.

6. The condom of claim 4, wherein said tubular member and said means defining said sealed chambers comprises a material which is fluid-tight to said rheopexic material laminated or bonded to said lambskin.

7. The condom of claim 6, wherein said laminated material comprises Teflon.

8. The condom of claim 6, wherein said laminated material comprises aluminum foil.

9. The condom of claim 5, wherein said means defining said tubular member and said means defining said sealed chambers comprises a material which is fluid-tight to said rheopexic material laminated or bonded to said lambskin.

10. The condom of claim 9, wherein said laminated material comprises Teflon.

11. The condom of claim 9, wherein said laminated material comprises aluminum foil.

12. The condom of claim 1 or claim 2, wherein at least one of said means defining said tubular member and said means defining said plurality of chambers is made of a thin layer of polyethylene.

13. The condom of claim 1 or claim 2, wherein at least one of said means defining tubular member and said means defining said plurality of chambers is made of a thin layer of polypropylene glycol.

14. The condom of claim 1 or claim 2, wherein said deformable sealed chambers are distributed around the circumference of said tubular member over said portion of the length of said tubular member.

15. The condom of claim 14, wherein said deformable fluid chambers are elongated sealed chambers oriented in the direction of the length of said tubular member, adjacent sealed chambers being offset or staggered with respect to each other.

16. A penis stiffening device comprising:
   means defining an elongated generally tubular member of thin, flexible material;
   means defining at least one deformable sealed chamber in said elongated tubular member;
   rheopexic fluid filled in said at least one deformable sealed chamber such that when said deformable sealed chamber is deformed during use, shear stress is applied to said rheopexic fluid due to deformation of said sealed chamber to cause said rheopexic fluid to increase its consistency as a function of increasing shear stress supplied thereto, thereby providing a stiffening effect to said elongated tubular member; and
   means for coupling said elongated tubular member to a penis.

17. The penis stiffening device of claim 16, wherein said generally tubular member comprises a plurality of deformable sealed chambers, rheopexic fluid be filled in said plurality of deformable sealed chambers.

* * * * *